US009719985B2

United States Patent
Witten

(10) Patent No.: US 9,719,985 B2
(45) Date of Patent: *Aug. 1, 2017

(54) METHOD OF DETECTION AND RELATED DETECTION DEVICE

(75) Inventor: Mark L. Witten, Tucson, AZ (US)

(73) Assignee: THE ARIZONA BOARD OF REGENTS ON BEHALF OF THE UNIVERSITY OF ARIZONA, Tucson, AZ (US)

(*) Notice: Subject to any disclaimer, the term of this patent is extended or adjusted under 35 U.S.C. 154(b) by 323 days.

This patent is subject to a terminal disclaimer.

(21) Appl. No.: 13/388,656

(22) PCT Filed: Aug. 2, 2010

(86) PCT No.: PCT/US2010/044099
§ 371 (c)(1),
(2), (4) Date: Feb. 2, 2012

(87) PCT Pub. No.: WO2011/017257
PCT Pub. Date: Feb. 10, 2011

(65) Prior Publication Data
US 2012/0135398 A1  May 31, 2012

Related U.S. Application Data

(60) Provisional application No. 61/273,243, filed on Aug. 3, 2009, provisional application No. 61/322,134, filed on Apr. 8, 2010.

(51) Int. Cl.
G01N 33/53 (2006.01)
G01N 33/569 (2006.01)
G01N 33/52 (2006.01)

(52) U.S. Cl.
CPC ....... *G01N 33/5308* (2013.01); *G01N 33/569* (2013.01); *G01N 33/521* (2013.01); *Y10T 436/163333* (2015.01); *Y10T 436/177692* (2015.01); *Y10T 436/182* (2015.01); *Y10T 436/19* (2015.01); *Y10T 436/200833* (2015.01); *Y10T 436/204998* (2015.01); *Y10T 436/214* (2015.01)

(58) Field of Classification Search
CPC ............ C12N 2320/10; C12N 2320/00; Y10T 436/163333; Y10T 436/204998; G01N 33/521; G01N 33/5308; G01N 33/54366; G01N 33/569
USPC .......................................... 422/501; 210/631
See application file for complete search history.

(56) References Cited

U.S. PATENT DOCUMENTS

| 8,628,625 | B2 * | 1/2014 | Witten | ................. G01N 33/521 134/10 |
| 2007/0269662 | A1 * | 11/2007 | Lopez et al. | ................... 428/446 |
| 2009/0011001 | A1 * | 1/2009 | Ahmad et al. | ................. 424/450 |

(Continued)

FOREIGN PATENT DOCUMENTS

WO  WO 2007125217 A1 * 11/2007
WO  WO 2009016366 A1 * 2/2009

*Primary Examiner* — Lyle Alexander
*Assistant Examiner* — Bryan Kilpatrick

(57) ABSTRACT

A method uses an Dioleoylphosphatidylcholine (DOPC) surfactant based bio film that reacts with a material in a known manner, and a device that utilizes such a biofilm, to detect material of interest is provided. The principles of the present invention are particularly useful in detecting/measuring a material.

25 Claims, 4 Drawing Sheets

(56) References Cited

U.S. PATENT DOCUMENTS

2009/0285867 A1\* 11/2009 Lesieur nee Boivin
et al. ............................ 424/401
2010/0216118 A1\* 8/2010 Witten .............................. 435/5

\* cited by examiner

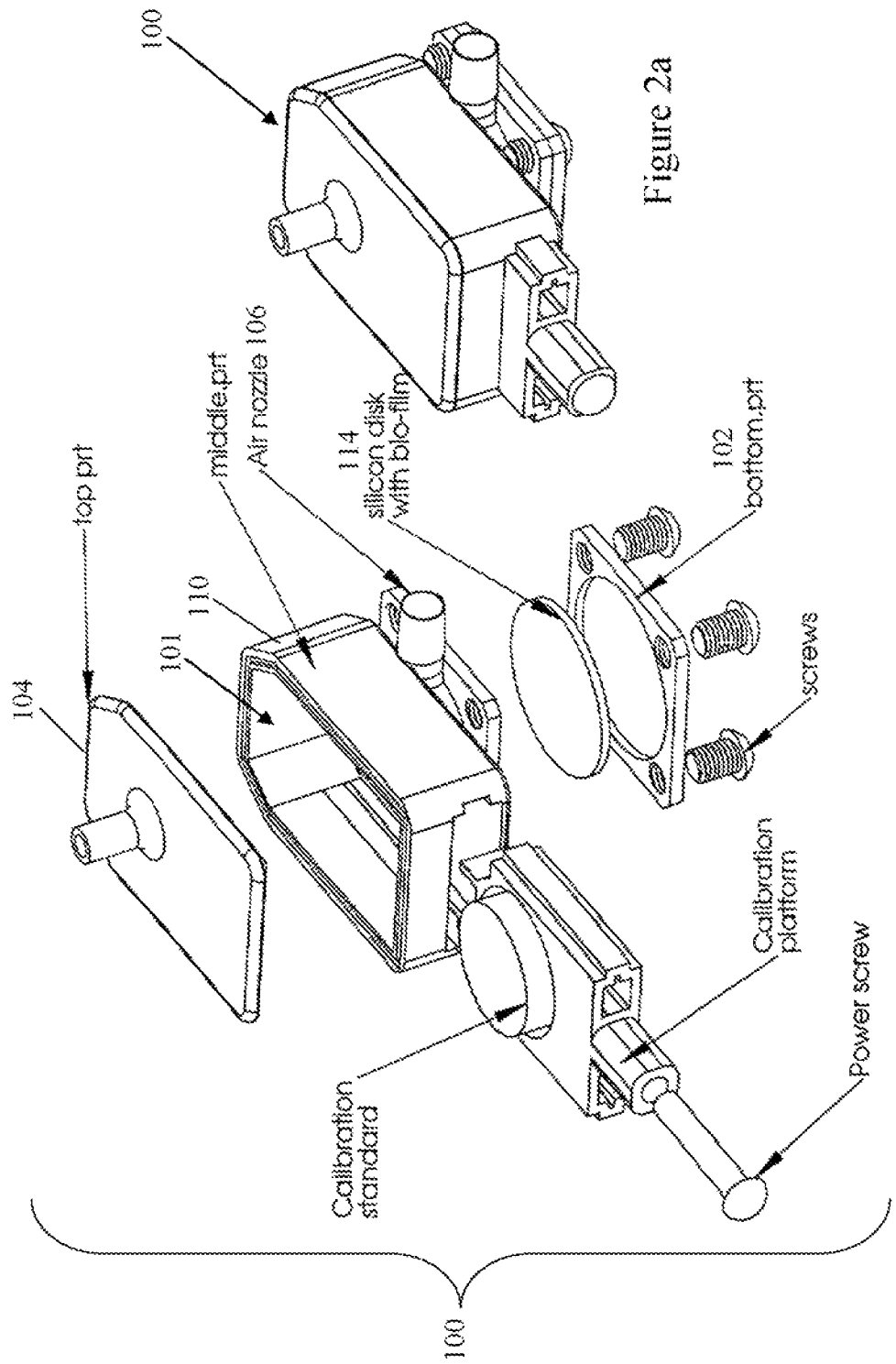

METHOD OF DETECTION AND RELATED DETECTION DEVICE

GOVERNMENT RIGHTS

This invention was made with government support under Research grant F49620-00-0119 awarded by the United States Air Force Office of Scientific Research. The government has certain rights in the invention.

RELATED APPLICATION/CLAIM OF PRIORITY

This application is a national stage application under 35 U.S.C. §371 of International Application No. PCT/US2010/044099, filed 2 Aug. 2010, which claims priority from and is entitled to the benefit of U.S. Provisional Application Nos. 61/273,243 filed 3 Aug. 2009 and 61/322,134 filed 8 Apr. 2010, all of which are herein incorporated by reference in their entireties.

BACKGROUND

In PCT application number PCT/US2007/00101, and US national stage application (Ser. No. 12/681,035) of PCT application number PCT/US2007/00101, filed on Mar. 31, 2010, applicant disclosed a biosensor and detection method using an L-α-dipalmitoleoyl-phosphatidylcholine (DPPC) surfactant based biosensor, and both U.S. application Ser. No. 12/681,035 and PCT application number PCT/US2007/00101 are incorporated by reference herein. A copy of PCT application number PCT/US2007/00101 is Exhibit B hereto.

SUMMARY OF THE INVENTION

The present invention relates to a new and useful method for detection of an airborne material that is harmful or dangerous to a human or to property, that uses a Dioleoyl-phosphatidylcholine (DOPC) surfactant based biofilm to detect for an airborne material of interest (e.g. airborne material(s) that can be harmful or dangerous to a human being or to property), and to a detection device that can be used in such method. The method and detection device are designed to detect, e.g., air borne bacteria, explosive vapors, gases and chemicals, and are also capable of detecting various additional harmful or dangerous materials of the types described in U.S. application Ser. No. 12/681,035 and PCT application number PCT/US2007/00101 (Exhibit B).

In its preferred form, the invention provides a DOPC surfactant based biofilm, whose configuration can be designed to detect and/or measure the presence and/or concentration of the material, by the change in state of the surfactant based biofilm when exposed to the material. For example, the DOPC surfactant based biofilm is designed to change its shape (e.g. its thickness) when exposed to the material.

In a method according to the present invention, a sensor with the DOPC surfactant based biofilm is exposed to an airborne fluid (e.g. an aerosol, vapor, or combination of aerosol and vapor) containing the material, and is used to detect or measure the concentration of the material. The DOPC surfactant based biofilm will change state (i.e. it changes thickness) in a characteristic way when exposed to a fluid containing the material, and by analyzing the change in the state of the biofilm, e.g. with a white light measuring system, characteristic changes in the state of the DOPC surfactant based biofilm can be used to detect the presence of, or measure the concentration of, the material in the airborne fluid.

In a method of reacting a material with a surfactant based biofilm, according to the principles of the present invention, a reactive device is provided, that comprises a DOPC surfactant based biofilm that is known to react with the material in the predetermined manner when the DOPC surfactant based biofilm is exposed to the material. The DOPC surfactant based biofilm is exposed to the material to enable the reaction with the material to occur in the predetermined manner. When the surfactant based biofilm is used as a sensor/detector, the effect on the state of the biofilm is then determined to identify the presence and/or concentration of the material.

Whether the method involves detection or measurement of the material, the DOPC surfactant based biofilm is generally exposed to an airborne fluid containing the material to produce the reaction.

When the method involves detection or measurement of the material, the DOPC surfactant based biofilm is characterized in that it has a predetermined state when not exposed to the material and changes state in a characteristic manner when exposed to the material (e.g. the state of the biofilm, as determined by spectrometric analysis, changes in a characteristic manner). Moreover, the change in state of the biofilm can also be a measure of the concentration of the material in the airborne fluid. A particularly useful feature of a detection process using a DOPC surfactant based biofilm is that with materials of interest the biofilm will change state in a characteristic way, depending on the material being detected, and when the material is removed from the environment of the biofilm, the biofilm will return substantially to its original state (i.e. a spectrometric analysis curve of the biofilm after the material is removed will be within about 95% of its original analysis curve), so that the surfactant based biofilm can be reused to detect the material.

When the surfactant based biofilm is being used to detect or measure the material, the DOPC surfactant based biofilm preferably has a thickness of about 200 Angstroms when not exposed to the material.

In one of its important detection/measurement aspects, the surfactant based biofilm is designed to react in the predetermined (characteristic) manner when exposed to a material in the fluid that includes any or all of the following genres of airborne material to produce the reaction: a bacteria that is harmful to humans and/or property, and explosive materials. The bacteria includes any or all of MRSA, *Staph Aureous*, and *Staph Epidermidis*, and the explosive vapors include any or all of TNT, PETN, RDX, nitrates and chlorates. The surfactant based biofilm is designed to detect the bacteria to the 30 CFU (colony forming unit) level, and to detect the explosive vapors at levels at concentrations of as little as 1.5 grams.

In another of its important aspects, the DOPC surfactant based biofilm is also designed to react in the predetermined manner when exposed to an airborne material that includes any or all of the following material to produce the reaction: carbon dioxide, methane, and nitric oxide. The surfactant based biofilm is designed to detect such materials at levels of concentration of as little as 20 ppm (parts per million).

The method and sensor of the present invention are also designed to detect the types of materials that the DPPC surfactant of PCT application number PCT/US2007/00101 (Exhibit B) are designed to detect. Specifically, the method and sensor are designed such that the surfactant based biofilm is exposed to a material in the fluid that includes any or all of the following genres of material to produce the reaction: a hydrocarbon that is harmful to a human lung, a hydrocarbon fuel, a biological and/or chemical warfare agent, a hydrocarbon-based solvent, an airborne metal that includes any or all of tungsten, arsenic and cobalt, a radioactive material, a gas containing nitric oxide, carbon dioxide or methane, a virus, engine oil vapors. More specifically, the radioactive material includes 99 m Tc DTPA; the hydrocarbon solvent includes any or all of ethanol, methanol, and acetone; the hydrocarbon fuel includes any or all of jet fuel, S-8 synthetic jet fuel, gasoline, diesel, kerosene; the biological and/or chemical warfare agent comprises any or all of ricin, sarin, anthrax, phosgene gas and mustard gas; and the virus includes A/8/68 Hong Kong Influenza virus.

Other features of the present invention will become further apparent from the following detailed description and the accompanying drawings.

BRIEF DESCRIPTION OF THE DRAWINGS

FIG. 2a is a schematic illustration of the detection/measurement chamber, and FIG. 2b is an exploded schematic illustration of the components of the detection/measurement chamber, that includes the detection/measurement device of the present invention, and which can be used in the practice of the method of the present invention;

DETAILED DESCRIPTION

Figures 1A, 1B:
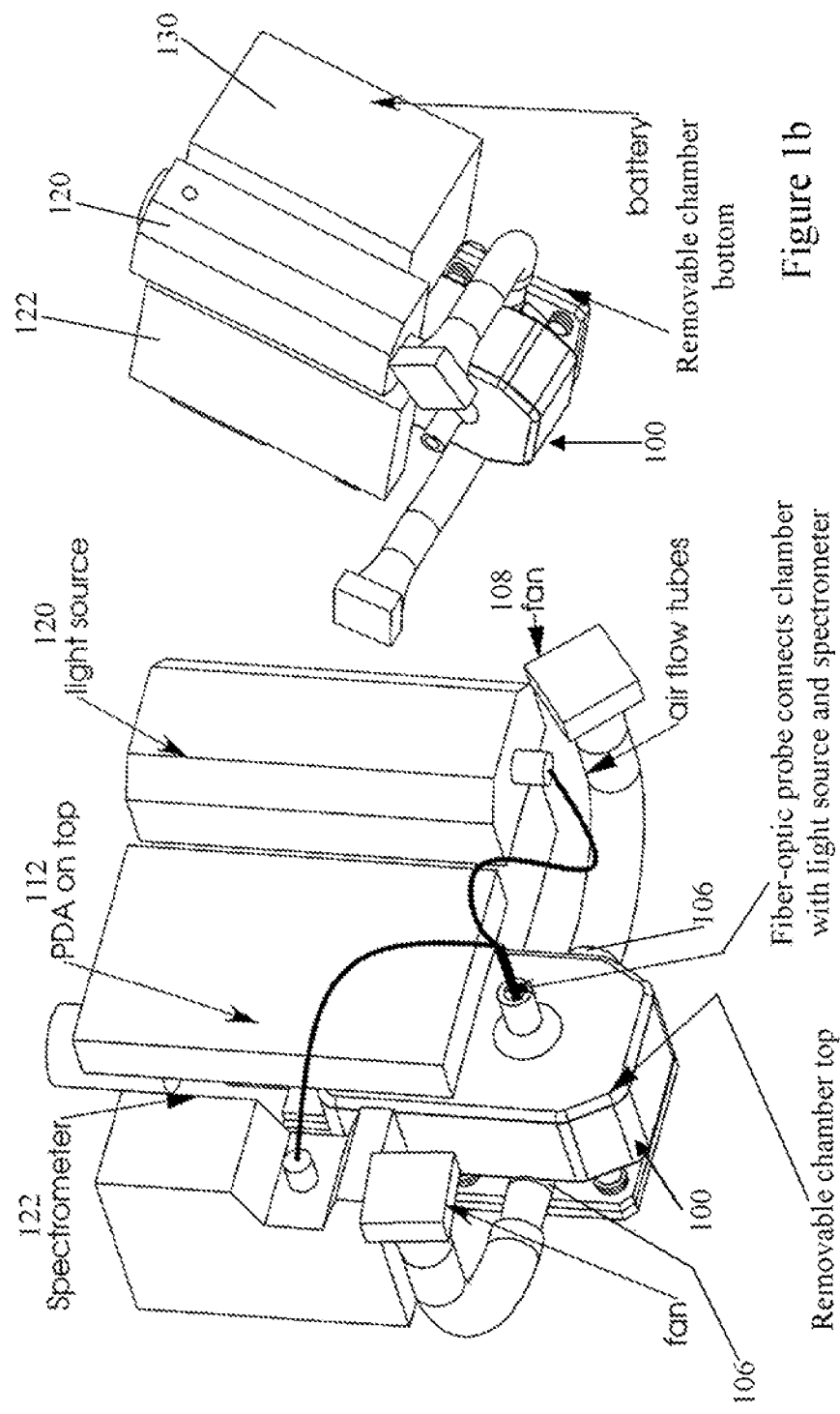
FIGS. 1a and 1b are schematic illustrations of a system with a DOPC biofilm sensor device, according to the principles of the present invention, and designed to practice a detection method according to the principles of the present invention.
Figure 3:
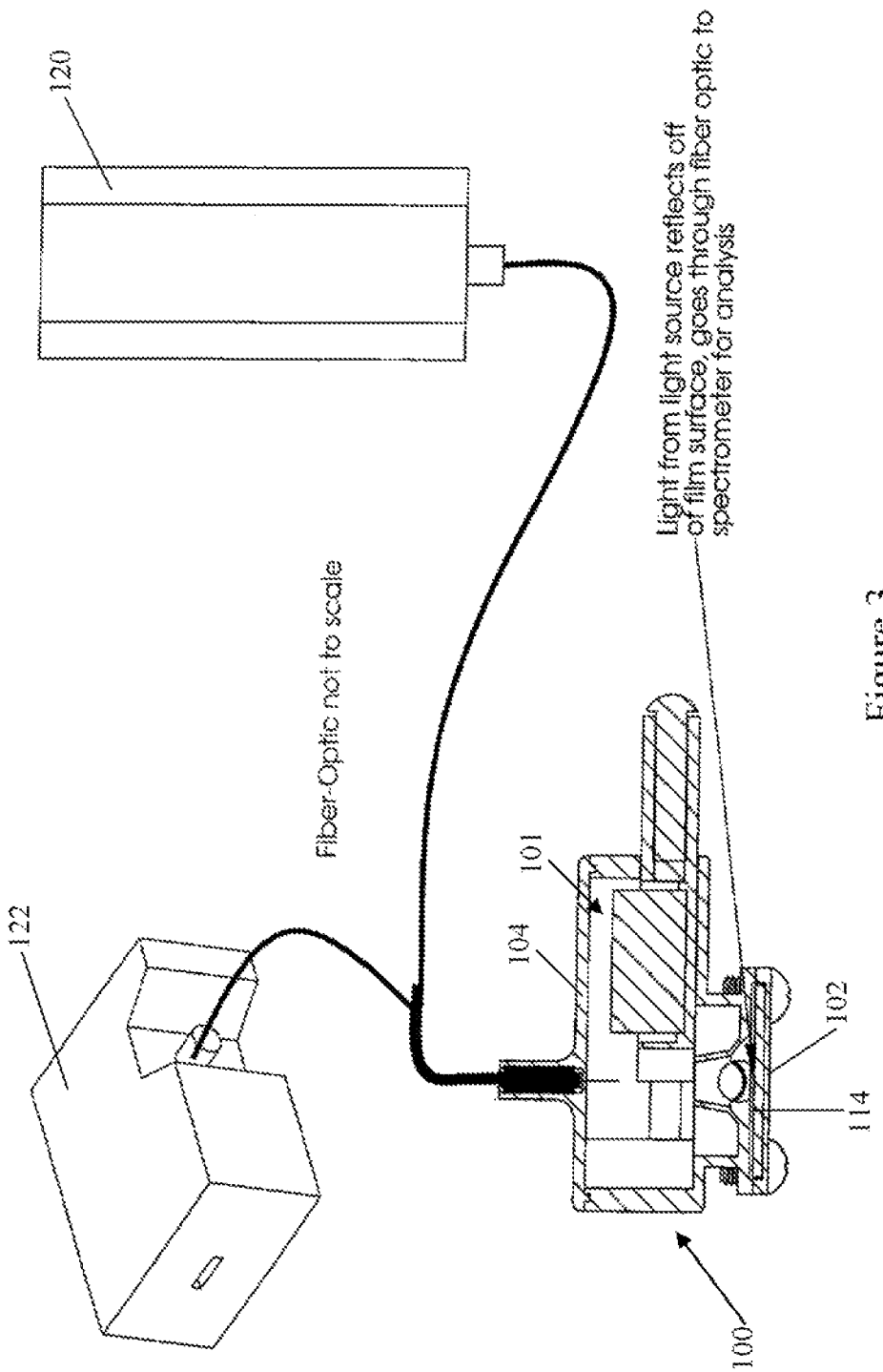
FIG. 3 is a schematic illustration of the light pathway schematic of the detection/measurement system that includes the detection/measurement device of the present invention, and that can be used in the practice of the method of the present invention.

As discussed above, the present invention relates to a new and useful sensor and method for detecting and/or measuring a material, using a DOPC surfactant based material. DOPC is a thermally stable phospholipid surfactant (and is referred to herein as a DOPC surfactant). The DOPC surfactant is preferably applied to a substrate (e.g. an oxidized silica, unoxidized silica, 50 micron gold coated silica and/or stainless steel substrate) to form a surfactant based biofilm. The DOPC surfactant can be of a type distributed by Lipoid (Germany).

An example of the manner in which a DOPC surfactant based biofilm, for a method and device according to the principles of the present invention is as follows: 100 milligrams of Dioleoylphosphatidylcholine (18:1/18:1) mixed with 2 mls each of acetone and chloroform. This mixture is then placed on a 2-inch diameter silicon disk and spun at 3000 rpm for 30 seconds. Other aspects of the preparation of the surfactant based biofilm, i.e. the preparation of the substrate, application of the surfactant, the acetone and/or the chloroform to the substrate, the equipment used to spin the substrate, and the post application examination of the surfactant coated substrate for irregularities, are all described in U.S. application Ser. No. 12/681,035 and PCT application number PCT/US2007/00101 (and Exhibit B), which have been incorporated by reference herein. The resulting surfactant based biofilm is approximately 200 Angstroms in thickness, and is substantially uniform in thickness with a smooth mirror like finish (meaning that to the naked eye the surface that will function as the detector for the material(s) of interest appears to be uniform with no appearance of blotchiness or patchiness).

A sensor device, according to the principles of the present invention, is shown in FIGS. 1a, 1b, 2a, 2b, 3 and 4 and is designed for use in exposing airborne fluids to the DOPC surfactant based biofilm, to enable the materials of interest to be detected. The device includes a cylindrical exposure chamber 101 that is 2.20 cm in diameter and 5.00 cm deep. An aluminum plate 102 is attached to the bottom of the chamber using standard screws and a rubber o-ring to create an air-tight seal. A removable 0.635 cm thick transparent glass plate 104 is then affixed to the topside of the chamber using silicon vacuum grease as a sealant. The chamber's volume is about 73.98 cm2. Two 0.635 cm National Pipe. Thread (NPT) holes 106 are positioned at 90 and 270 degrees opposite each other through the central column in the block 110 that forms the housing of the chamber, which serves as inlet and outlet holes for organic compound saturated N2 flows. A fan 108 is used to control the flow of fluid (air) through the chamber 100. The surfactant based biofilm is placed in a holder which allows a 2-8 liter/minute airflow across the surfactant based biofilm. A tungsten white light system (400 nm to 850 nm range) shines on the biofilm and the signal is then reflected back to a spectrometer (e.g. art Ocean Optics model number UBS 2000) that divides the light signal into a wavelength of 300 nm to 1200 nm in 2048 data points. This information is then fed into an Ocean Optics computer program (e.g. an Ocean Optics Spectral Suite program that can be [downloaded from the Ocean Optics website, www.oceanoptics.com] obtained from Ocean Optics) that generates signal curves from the sensor with intensity measured on the Y-axis and wavelength on the X-axis. A device such as a PDA 112 can provide a user interface.

Figure 4:
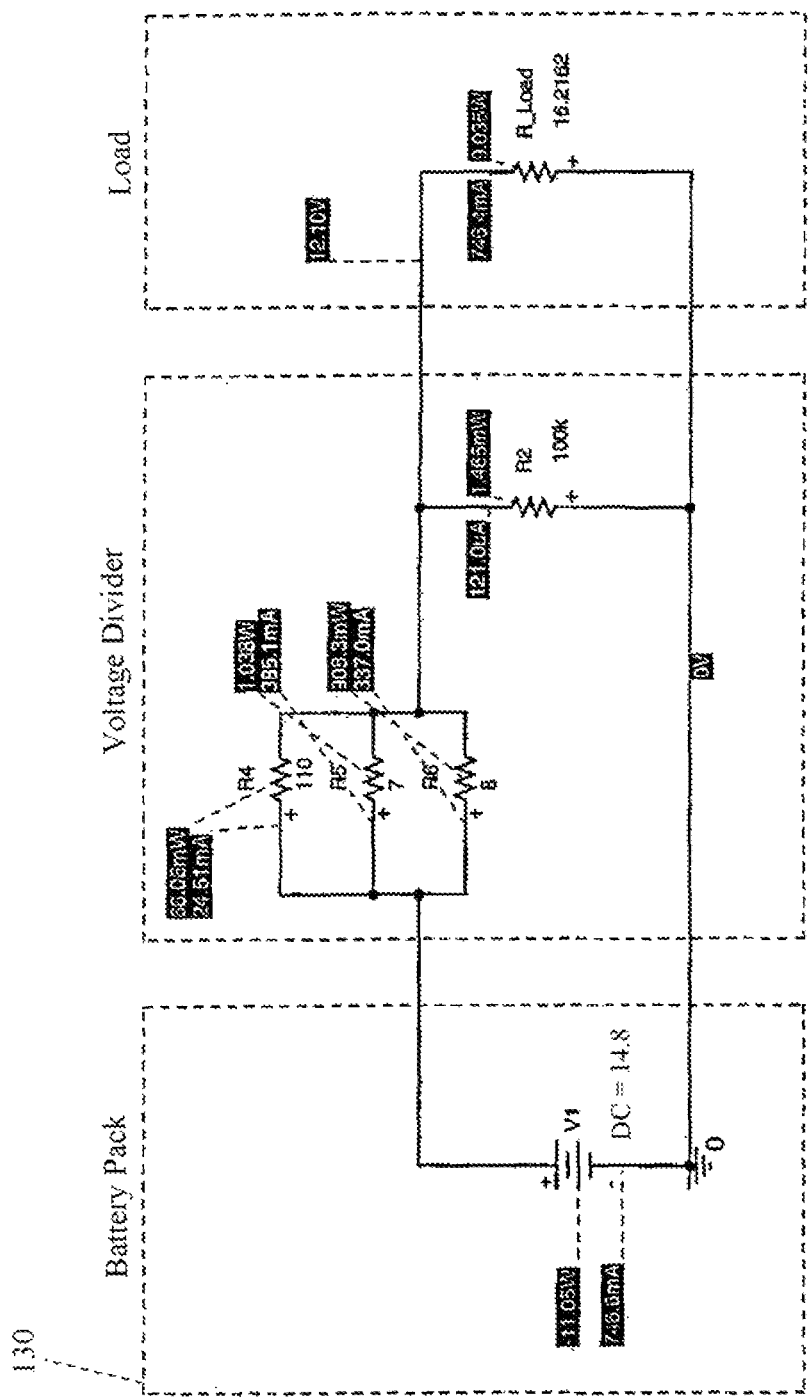
FIG. 4 shows the electrical wiring diagram of the detection/measurement system that can be used in the practice of the method of the present invention.

The circuit shown in FIG. 4 is powered by a battery 130 used to control the air fan 108, the light source 120, and the PDA 112. Film thickness is determined by measuring interference between incident and reflected light through the DOPC film/substrate film layers. The resulting data is used by the Ocean Optics Spectral Suite program to compute the total optical thickness of the DOPC film and substrate. The DOPC film thickness is then calculated by taking the difference between the total thickness of the DOPC film sensor and substrate.

Further aspects of the manner in which the sensor device described above and in U.S. application Ser. No. 12/681,035 and PCT application number PCT/US2007/00101, which have been incorporated by reference herein, can be tested, calibrated and operated, are described in those applications (and in Exhibit B hereto).

Thus, a detection system has been developed where the DOPC surfactant based biofilm can be exposed to a material of interest (that is contained in an airborne fluid sample) and used to detect the material of interest. The detection system utilizes a DOPC surfactant based biofilm on a substrate, and is useful in detecting the presence of a material of interest in an airborne fluid sample. A sensor, constructed in accordance with the principles of the system shown in FIGS. 1a, 1b, 2a, 2b, 3 and 4 (and described above), is designed be effective to detect a number of materials of interest and also to measure the concentrations of a number of materials.

In a method according to the present invention, a sensor with the (DOPC) surfactant based biofilm is exposed to an aerosol or vapor containing the material, and is used to detect or measure the concentration of the material. The DOPC surfactant based biofilm has been found to change state (i.e. it the signal curves measured by spectrometrical analysis will change in a characteristic way) when exposed to an aerosol or vapor containing the material, and by analyzing the state of the biofilm, e.g. with a white light measuring system, characteristic changes in the state of the DOPC surfactant based biofilm can be used to detect the presence of, or measure the concentration of, the material in the vapor or aerosol.

In a method of reacting a material with a surfactant based biofilm, according to the principles of the present invention, a reactive device is provided, that comprises a substrate with a DOPC surfactant based biofilm that is known to react with a material in the predetermined manner when the DOPC surfactant based biofilm is exposed to the material. The DOPC surfactant based biofilm is exposed to the material to enable the reaction with the material to occur in the predetermined manner, and the effect on the biofilm is then determined to identify the presence and/or concentration of the material.

Whether the method involves detection or measurement of the material the DOPC surfactant based biofilm is generally exposed to an airborne fluid (aerosol, vapor, or combination of aerosol and vapor) containing the material to produce the reaction.

When the method involves detection or measurement of the material, the DOPC surfactant based biofilm is characterized in that it has a predetermined state (e.g. thickness) when not exposed to the material and changes state in a predetermined manner (as determined by a change in spectral curves) when exposed to the material. A particularly useful feature of a detection process using a biofilm based on a DOPC surfactant is that with most materials of interest the biofilm will not only change state, in a characteristic way, depending on the material being detected, and when the material is removed from the environment of the biofilm, the biofilm will return substantially to its original state (i.e. its spectral curve will return to a state that is within least 95% of its original spectral curve), so that the substrate can be reused to detect the material(s) of interest.

When the biofilm is being used to detect or measure the material, the DOPC surfactant based biofilm preferably has a thickness of about 200 Angstroms when not exposed to the material (meaning that the application process is targeted to provide a biofilm at a 200 Angstrom thickness).

In one of its important detection/measurement aspects, the surfactant based biofilm is designed to react in the predetermined (characteristic) manner when exposed to a material in the fluid that includes any or all of the following genres of airborne material to produce the reaction: a bacteria that is harmful to humans and/or property, and explosive materials. The bacteria includes any or all of MRSA, *Staph Aureous*, and *Staph Epidermidis*, and the explosive vapors include any or all of TNT, PETN, RDX, nitrates and chlorates. The surfactant based biofilm is designed to detect the bacteria to the 30 CFU (colony forming unit) level, and to detect the explosive vapors at levels at concentrations of as little as 1.5 grams.

The method and sensor of the present invention are also designed to detect the types of materials that the DPPC surfactant of PCT application number PCT/US2007/00101 (Exhibit B) are designed to detect. Specifically, the method and sensor are designed such that the surfactant based biofilm is exposed to a material in the fluid that includes any or all of the following genres of material to produce the reaction: a hydrocarbon that is harmful to a human lung, a hydrocarbon fuel, a biological and/or chemical warfare agent, a hydrocarbon-based solvent, an airborne metal that includes any or all of tungsten, arsenic and cobalt, a radioactive material, a gas containing nitric oxide, carbon dioxide or methane, a virus, engine oil vapors. More specifically, the radioactive material includes 99 m Tc DTPA; the hydrocarbon solvent includes any or all of ethanol, methanol, and acetone; the hydrocarbon fuel includes any or all of jet fuel, S-8 synthetic jet fuel, gasoline, diesel, kerosene; the biological and/or chemical warfare agent comprises any or all of ricin, sarin, anthrax, phosgene gas and mustard gas; and the virus includes A/8/68 Hong Kong Influenza virus With the foregoing disclosure in mind, it is believed that various adaptations of the use of a DOPC surfactant based device and method that reacts with a material in a known manner, to detect a material of interest or to extract a material of interest from a material, will be apparent to those in the art.

The invention claimed is:

1. A method of reacting a material with a surfactant based biofilm and detecting the reaction of the material, comprising (a) providing a reactive structure comprising a substrate with a surfactant based biofilm that is known to change shape as determined by light reflectivity and/or reflective light scattering methods when the surfactant based biofilm is exposed to the material, the surfactant based biofilm comprising a DOPC surfactant based biofilm; (b) exposing the surfactant based biofilm to the material to produce the reaction with the material in the predetermined manner, and (c) detecting the reaction of the material with the surfactant based biofilm by directing light at the material with the surfactant based biofilm and detecting the light reflected from or scattered by the material with the surfactant based biofilm.

2. The method of claim 1, wherein the surfactant based biofilm is exposed to an airborne fluid containing the material to produce the reaction.

3. The method of claim 2, wherein the surfactant based biofilm is characterized in that it has a predetermined state when not exposed to the material and changes state in a predetermined manner when exposed to the material.

4. The method of claim 2, wherein the surfactant based biofilm has a thickness of about 200 Angstroms when not exposed to the material.

5. The method of claim 4, wherein the surfactant based biofilm is exposed to a material in the fluid that includes any or all of the following genres of airborne material to produce the reaction: a bacteria that is harmful to humans, and explosive materials.

6. The method of claim 5, wherein the bacteria includes any or all of MRSA, *Staph Aureous*, and *Staph Epidermidis*, and the explosive vapors include any or all of TNT, PETN, RDX, nitrates and chlorates.

7. The method of claim 6, wherein the surfactant based biofilm can detect the bacteria to the 30 CFU level.

8. The method of claim 6, wherein the surfactant based biofilm can detect the explosive vapors at levels as little as 1.5 grams.

9. The method of claim 4, wherein the surfactant based biofilm is exposed to an airborne material that includes any or all of the following material to produce the reaction: carbon dioxide, methane, and nitric oxide.

10. The method of claim 9, wherein the surfactant based biofilm can detect the material to about a 20 ppm concentration.

11. The method of claim 4, wherein the surfactant based biofilm is exposed to a material in the fluid that includes any or all of the following genres of material to produce the reaction: a hydrocarbon that is harmful to a human lung, a hydrocarbon fuel, a biological and/or chemical warfare agent, a hydrocarbon-based solvent, an airborne metal that includes any or all of tungsten, arsenic and cobalt, a radioactive material, a gas containing nitric oxide, carbon dioxide or methane, a virus, engine oil vapors.

12. The method of claim 11, wherein the radioactive material includes 99m Tc DTPA; the hydrocarbon solvent includes any or all of ethanol, methanol, and acetone; the hydrocarbon fuel includes any or all of jet fuel, S-8 synthetic jet fuel, gasoline, diesel, kerosene; the biological and/or chemical warfare agent comprises any or all of ricin, sarin, anthrax, phosgene gas and mustard gas; and the virus includes A/8/68 Hong Kong Influenza virus.

13. A sensor comprising a substrate with a surfactant based biofilm thereon, the surfactant based biofilm characterized by its ability to change shape as determined by light reflectivity and/or reflective light scattering methods when the surfactant based biofilm is exposed to the material, the surfactant based biofilm comprising a DOPC surfactant based biofilm, and the sensor configured to direct light at the material with the surfactant based biofilm and to detect the light reflected from or scattered by the material with the surfactant based biofilm.

14. The sensor of claim 13, wherein the surfactant based biofilm is characterized in that it has a predetermined state when not exposed to the known material and changes state in a predetermined manner when exposed to the known material.

15. The sensor of claim 14, wherein the surfactant based biofilm is further characterized in that it will return substantially to its original state when exposure to the known material is discontinued.

16. The sensor of claim 13, wherein the surfactant based biofilm has a thickness of about 200 Angstroms when not exposed to the known material.

17. The sensor of claim 16, wherein the surfactant based biofilm is exposed to a material in the fluid that includes any or all of the following genres of airborne material to produce the reaction: a bacteria that is harmful to humans, and explosive materials.

18. The sensor of claim 17, wherein the bacteria includes any or all of MRSA, *Staph Aureous*, and *Staph Epidermidis*, and the explosive vapors include any or all of TNT, PETN, RDX, nitrates and chlorates.

19. The sensor of claim 17, wherein the surfactant based biofilm is characterized in that it can detect the bacteria to the 30 CFU level.

20. The sensor of claim 17, wherein the surfactant based biofilm can detect the explosive materials at levels as little as 1.5 grams.

21. The sensor of claim 16, wherein the surfactant based biofilm is exposed to an airborne material that includes any or all of the following material to produce the reaction: carbon dioxide, methane, and nitric oxide.

22. The sensor of 21, wherein the surfactant based biofilm can detect the material to about a 20 ppm concentration.

23. The sensor of claim 16, wherein the surfactant based biofilm is exposed to a material that includes any or all of the following genres of material to produce the reaction: a hydrocarbon that is harmful to a human lung, a hydrocarbon fuel, a biological and/or chemical warfare agent, a hydrocarbon-based solvent, an airborne metal that includes any or all of tungsten, arsenic and cobalt, a radioactive material, a gas containing nitric oxide, carbon dioxide or methane, a virus, engine oil vapors.

24. The sensor of claim 23, wherein the radioactive material includes 99m Tc DTPA; the hydrocarbon solvent includes any or all of ethanol, methanol, and acetone; the hydrocarbon fuel includes any or all of jet fuel, S-8 synthetic jet fuel, gasoline, diesel, kerosene; the biological and/or chemical warfare agent comprises any or all of ricin, sarin, anthrax, phosgene gas and mustard gas; and the virus includes A/8/68 Hong Kong Influenza virus.

25. The sensor of claim 13, wherein the surfactant based biofilm is located in a chamber, a light source that directs light at the surfactant based biofilm is directed into the chamber, and a conduit directs the light reflected from or scattered by the material with the surfactant based biofilm from the chamber to a device that detects the light reflected from or scattered by the material.

* * * * *